United States Patent
Nufer et al.

(10) Patent No.: US 9,418,419 B2
(45) Date of Patent: Aug. 16, 2016

(54) CONTROL METHOD AND APPARATUS TO PREPARE MEDICAL IMAGE DATA WITH USER ACCEPTANCE OF PREVIEWS AFTER EACH OF FIRST AND SECOND FILTERING OF THE MEDICAL IMAGE DATA

(71) Applicant: Siemens Aktiengesellschaft, Munich (DE)

(72) Inventors: Stephan Nufer, Erlangen (DE); Andreas Prause, Erlangen (DE)

(73) Assignee: Siemens Aktiengsellschaft, Munich (DE)

( * ) Notice: Subject to any disclaimer, the term of this patent is extended or adjusted under 35 U.S.C. 154(b) by 22 days.

(21) Appl. No.: 14/460,503

(22) Filed: Aug. 15, 2014

(65) Prior Publication Data

US 2015/0049927 A1    Feb. 19, 2015

(30) Foreign Application Priority Data

Aug. 16, 2013 (DE) .......................... 10 2013 216 304

(51) Int. Cl.
| | |
|---|---|
| G06K 9/00 | (2006.01) |
| G06T 7/00 | (2006.01) |
| G06T 5/00 | (2006.01) |
| G06F 19/00 | (2011.01) |
| A61B 6/00 | (2006.01) |

(52) U.S. Cl.
CPC ............ *G06T 7/0012* (2013.01); *G06F 19/321* (2013.01); *G06T 5/001* (2013.01); *A61B 6/461* (2013.01); *G06T 2207/10072* (2013.01); *G06T 2207/20024* (2013.01); *G06T 2207/30004* (2013.01)

(58) Field of Classification Search
None
See application file for complete search history.

(56) References Cited

U.S. PATENT DOCUMENTS

| | | | | |
|---|---|---|---|---|
| 2002/0018592 | A1* | 2/2002 | Labelle | G06F 17/30256 382/165 |
| 2004/0136577 | A1* | 7/2004 | Rao | G06K 9/58 382/128 |
| 2004/0240720 | A1* | 12/2004 | Brantley | G06F 19/3487 382/132 |
| 2005/0117816 | A1* | 6/2005 | Saeger | G06F 17/30265 382/305 |
| 2007/0286519 | A1* | 12/2007 | Friedrich | G06T 5/20 382/260 |
| 2009/0154825 | A1* | 6/2009 | Yang | G06T 5/50 382/260 |
| 2012/0158709 | A1* | 6/2012 | Gaonkar | G06F 17/30156 707/723 |
| 2015/0049927 | A1* | 2/2015 | Nufer | G06F 19/321 382/128 |

* cited by examiner

*Primary Examiner* — Tahmina Ansari
(74) *Attorney, Agent, or Firm* — Schiff Hardin LLP

(57) ABSTRACT

Medical image data of at least one medical imaging apparatus are prepared in a computerized procedure wherein the medical image data are received by a reception unit, a first subset of the medical image data is selected by at least one first filter unit, the first subset of the medical image data is processed by at least one second filter unit, with the processing leading to a second subset, the second subset of the medical image data are sorted and/or grouped by the processing unit, a presentation type for the second subset of the medical image data is determined by means of the processing unit, and the second subset of the medical image data is presented as an output according to a defined presentation type by an output unit.

6 Claims, 1 Drawing Sheet

CONTROL METHOD AND APPARATUS TO PREPARE MEDICAL IMAGE DATA WITH USER ACCEPTANCE OF PREVIEWS AFTER EACH OF FIRST AND SECOND FILTERING OF THE MEDICAL IMAGE DATA

BACKGROUND OF THE INVENTION

1. Field of the Invention

The present invention concerns a computerized control method to prepare medical image data; a computer programmed for the execution of such a control method; and a non-transitory computer-readable storage medium encoded with programming instructions that cause such a control method to be implemented when the instructions are executed by a computer.

2. Description of the Prior Art

The preparation of medical image data is a widespread field of activity, in particular in clinical applications.

In the everyday clinical environment, a suitable preparation of medical image data (in particular for an efficient and goal-directed diagnosis) can represent an extremely complex problem, primarily if a number of medical image data sets are provided.

SUMMARY OF THE INVENTION

An object of the invention is to provide a method that facilitates the preparation of such medical image data and with which the presentation of the image data in a form necessary for making a medical diagnostic finding is possible depending on different boundary conditions.

A control method for preparation of medical image data from at least one medical imaging apparatus in accordance with the invention includes the following steps. The medical image data are received by a reception unit of a computerized control unit. A first subset of the medical image data is selected by filtering the received data in at least one first filter unit of the control unit. The first subset of the medical image data is processed by at least one second filter unit of the control unit, with the processing resulting in a second subset. The second subset of the medical image data is sorted and/or grouped by a processing unit of the control unit. A presentation type for the second subset of the medical image data is determined by the processing unit. The second subset of the medical image data emitted at an output unit of the control unit according to a defined presentation type.

The medical imaging apparatus is an apparatus (such as an electronic and/or information technology apparatus) to receive, process, evaluation and/or store image information in the form of image data. For example, acoustic methods such as ultrasound (US); emission methods such as emission computed tomography (ECT) and positron emission tomography (PET); optical methods; radiological methods such as x-ray tomography and radiological computed tomography (CT) can be used to acquire the image information. The acquisition can also take place by magnetic resonance tomography (MR or MRT) or by combined modalities. The medical imaging apparatus can supply 2-dimensional (2D) or multidimensional image data such as 3-dimensional (3D) or 4-dimensional (4D) image data that can be stored and/or processed in different formats. The medical imaging apparatus can be used for making a medical diagnosis.

The processing unit or a processor (central processing unit, CPU) is, for example, a microprocessor or digital signal processor (DSP). The processor (which is controlled by the program, which can be divided into a number of program modules) writes data into the storage, reads data from the storage and processes the data. For example, the processor can also be executed as an (application-specific) field programmable (logic) gate array (Field Programmable Gate Array, FPGA).

For example, the output unit can be a monitor to show options, commands, parameter data, sequence data and/or for graphical output of image data etc.

The receipt of the medical image data takes place via a reception unit. The reception unit can be fashioned as part of the processing unit. For example, reception is the loading of image data from a database or a transmission of image data from another source, but the reception can also include the actual procedure of acquiring the image data from a patient.

The selection of a first subset of the medical image data takes place in at least one first filter unit. The first filter unit includes at least one selection criterion with which the subset of the medical image data is determined. The subset can include the original set of image data. For example, such selection criteria include (but not exclusively) DICOM (Digital Imaging and Communications in Medicine) attributes, thus attributes of an open standard for storage and exchange of information in medical image data management, for instance properties of a contrast or an orientation, or other attributes, for instance points in time of a measurement or information about an administration of contrast agent. Different attributes can differ in different levels of scalability; for example, they can be nominally, ordinally or cardinally scalable. Due to the widespread use of the DICOM standard, a high degree of compatibility is present since the interoperability between systems of different manufacturers is possible.

The processing of the first subset of the medical image data takes place in at least one second filter unit, and this processing leads to a second subset. The second filter unit includes at least one processing rule with which the first subset of the medical image data is processed. For example, such processing rules include (but not exclusively) fusions, i.e. superpositions of image data; assemblies and thus combinations of image data; or subtractions, i.e. rules with which pixel and/or voxel values from image data are subtracted from one another. The second subset of the medical image data can also include the first subset of the medical image data entirely or in part, for instance if the results after application of the second filter to the medical image data are added to the results of the application of the first filter to the medical image data.

The sorting and/or grouping of the second subset of the medical image data takes place in the processing unit. The sorting includes an organization according to a predeterminable criterion such as, for example, an acquisition point in time, an image size or other values. The result of the sorting is thus a sequence of image data. The grouping includes a classification of image data in at least one class. Image data are associated with a class if they coincide in defined (likewise predeterminable) properties, for example an alignment with respect to the patient or another reference. The sorting and/or grouping can also include the omission of defined image data, for example if only a specific amount of image data is desired.

The determination of a presentation type for the second subset of the medical image data likewise takes place in the processing unit. The presentation type includes all possible forms of depicting image data, thus all possible presentation configurations. The presentation type essentially includes the number of images that should be provided to an output unit and the mode of how they should be provided to the output unit, such as whether a particular screen content item or field should be displaceable or not.

The presentation of the second subset of the medical image data according to a defined presentation type takes place exclusively at the output unit.

A preparation of medical image data according to the invention thus means a defined selection and/or arrangement and/or presentation and/or logic with regard to at least one requirement for the medical image data.

The invention utilizes a combination of two filter units each having at least one filter criterion in order to associate subsets of the medical image data (from a number of present medical image data) that are relevant to a creation of one or more findings. The medical image data are additionally brought into a defined logical order via sorting and/or grouping specifications.

In a preferred embodiment, the first subset of the medical image data is also made available as an output by the output unit. This output of the first subset preferably takes place directly after selecting the first subset of the medical image data in the at least one filter unit. With this type of preview, a user can directly perceive the result of the application of the first filter to the output unit. The preview preferably takes place in real time, thus within a predefined, fixed time interval.

In an embodiment, after the output of the first subset of the medical image data, a new selection of a new first subset of the medical image data is conducted, and the original selection is discarded. After receiving the result of the application of the first filter to the output unit, a user can thus adapt and/or refine the filter criteria. The method according to the invention thus repeats the step of selecting a first subset of the medical image data by the at least one first filter unit.

In another embodiment, only an initial processed image from the second subset of the medical image data is provided as an output by the output unit. Computing time thus can be saved, and the result of the determination of the presentation type can be received quickly.

In a further embodiment, after the first processed image is presented as an output a new determination of a presentation type is made for the second subset of the medical image data, and the original determination is discarded. In this way, changes and/or refinements to the determination of the presentation type can be made in a time-saving manner. The method according to the invention thus repeats determination step.

In a further embodiment, the determination of the presentation type of the medical image data includes the determination of an image format. As used herein, the image format is primarily the relationship of length to width of an image or of an image field. The presentation of the medical image data thus can be optimized for the output unit that is used.

In an embodiment according to the invention, the determination of the presentation type of the medical image data includes a synchronization of the medical image data with regard to defined attributes. As used herein, synchronization is the establishment of defined attributes, thus the establishment of defined properties for all medical image data of a defined type. For example, a predeterminable image section or zoom factor can be established for all image data with a defined orientation. In this way, the medical image data can be prepared such that, for example, the same image section is always perceivable, without such settings needing to be made manually for every image. This saves time in the processing of the medical image data as well as in the evaluation of the medical image data.

In a preferred embodiment, the determination of the presentation type of the medical image data includes a display of additional available information, for instance additional evaluations and/or examination results corresponding to the image data. This additional available information can be mean value curves of dynamic contrast measurements, for example. This additional available information can also be information that goes beyond the image data information, to the extent that such additional information can be loaded from a database. All available information is thereby presented to the user without needing to implement additional evaluations. This saves time and increases the precision of the finding.

In another embodiment, one or more of the reception of the medical image data, the selection of the first subset of the medical image data, the processing and/or sorting and/or grouping of the second subset of the medical image data, the determination of a presentation type for the subset of the medical image data, and the output of the second subset of the medical image data according to a defined presentation type, takes place automatically, i.e. by a preallocation of all settable parameters of the method, for example the type of sorting and/or grouping or the type of determination of the presentation type. Such a preallocation according to standard values leads to an additional time saving in the event that the same selection of parameters is always desired in many embodiments of the method according to the invention. The preallocation with standard values also serves for an optimized presentation of the results in the event that a user does not have knowledge about all method settings.

Within the scope of the present invention, a computerized control unit is also provided to prepare medical image data of at least one medical imaging apparatus.

The computerized control unit includes a reception unit that configured to receive the medical image data, a first filter unit configured to select a first subset of the medical image data, a second filter unit configured to process the first subset of the medical image data, which leads to a second subset, a processing unit configured to sort and/or group the second subset of the medical image data and to define a presentation type for the second subset of the medical image data, and an output unit at which the second subset of the medical image data is presented as an output according to a defined presentation type.

The present invention also encompasses a non-transitory, computer-readable data storage medium encoded with programming instructions that, when the storage medium is loaded into a computerized processor, cause the processor to implement any or all of the embodiments of the method according to the invention described above.

The programming instructions can be in source code that must still be compiled (translated) and linked or that only must be interpreted, or can be in the form of an executable software code that has only to be loaded into the corresponding computer for execution.

The electronically readable storage medium can be, for example, a DVD, a magnetic tape or a USB stick, on which is stored electronically readable control information, in particular software.

The advantages of the control unit according to the invention, and of the electronically readable storage medium according to the invention essentially correspond to the advantages of the control method according to the invention that have been described above. Features, advantages or alternative embodiments that are noted with regard to the method also apply to the other aspects of the invention. The corresponding functional features of the method are implemented by corresponding substantive modules, in particular by hardware modules.

DESCRIPTION OF THE PREFERRED EMBODIMENTS

Figure 1:
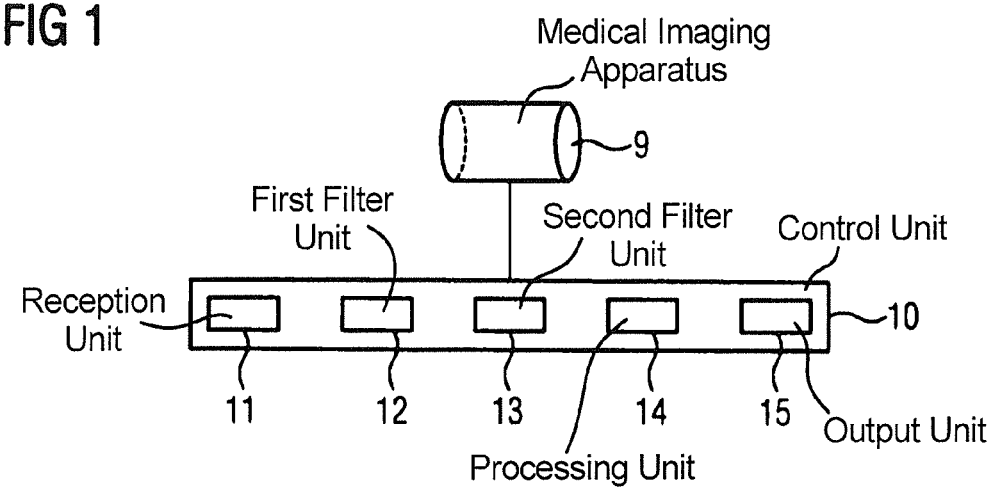
FIG. 1 is a block diagram of a control unit according to the invention.

FIG. 1 shows a control unit 10 according to the invention for preparation of medical image data of at least one medical imaging apparatus 9.

The control unit 10 includes:
- a reception unit 11 that is designed (configured) to receive the medical image data,
- a first filter unit 12 that is configured to select a first subset of the medical image data,
- a second filter unit 13 that is configured to process the first subset of the medical image data, which leads to a second subset,
- a processing unit 14 that is configured to sort and/or group the second subset of the medical image data and to define a presentation type for the second subset of the medical image data, and
- an output unit 15 at which the second subset of the medical image data is presented according to a defined presentation type.

The control unit 10 is connected with a medical imaging apparatus 9 and can directly access the measurement data of the medical imaging apparatus 9 and receive the medical image data according to method step 2. The loading of image data from a database is also possible via the reception unit 11. The control method with method steps 1 through 8 according to FIG. 1 can be executed with the control unit 10. It is designed as a processor unit, in particular as a graphics processor in a graphics card.

A database is a system for electronic data administration, in particular for storage, overwriting and deletion of data and to optimize queries to the database. The database offers a database language for such queries.

A memory unit comprises (for example) read-only memory (ROM) such as electrically erasable programmable read-only memory (EEPROM) or Flash EEPROM, read/write memory (random access memory, RAM) and disk storage such as hard drive storage. The memory unit can be used to store a program (for example an operating system or an application program) and/or data (in particular image data, instruction data, configuration data, parameter data, protocol data and sequence data).

An operating system includes computer programs, administers the system resources (hardware components) of a computer (for example memory units such as working memory and hard disks, input and output units such as interfaces) and provides application programs. The operating system thus forms an interface between the system resources and the application programs.

Figure 2:
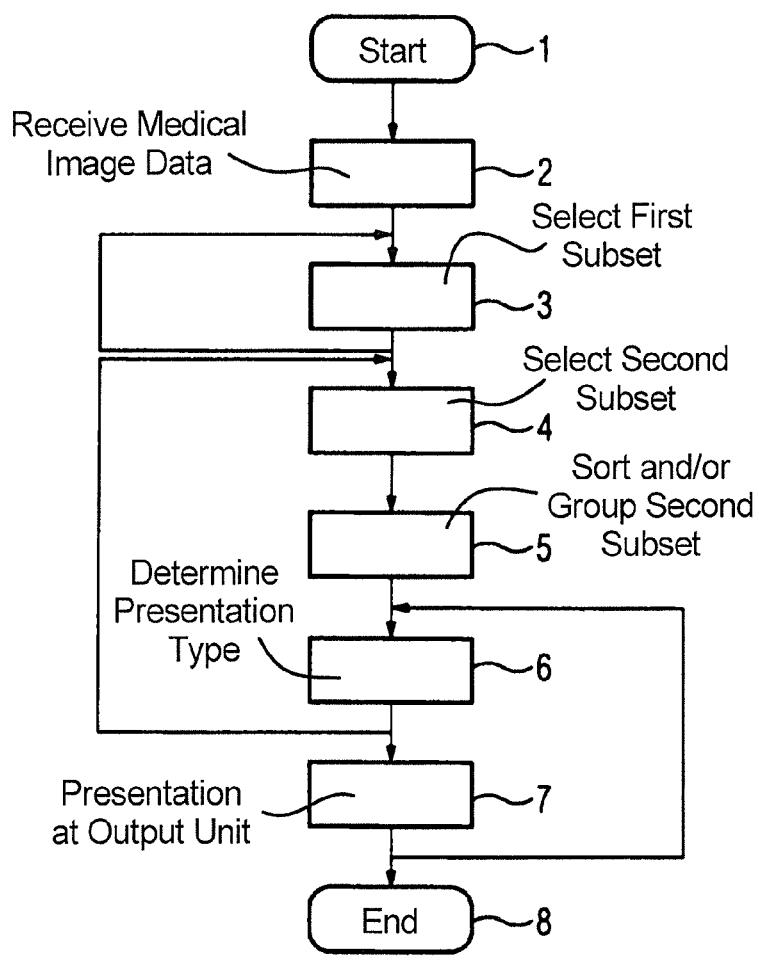
FIG. 2 is a flowchart of an embodiment of the control method according to the invention.

FIG. 2 shows a flowchart of an embodiment of the control method according to the invention. The control method includes the method steps 1 through 8, wherein specification portions including the corresponding reference characters introduced in connection with the other Figure are also used in the description of method steps 1 through 8.

Method step 1 designates the start of the preparation of medical image data of at least one medical imaging apparatus 9.

Medical image data are received in method step 2 by the reception unit 11. The reception unit 11 can also be fashioned as part of the processing unit 14. As used herein, "received" means the loading of image data from a database but can also include the actual process of acquiring the image data, for example via a magnetic resonance apparatus.

During the method step 3, the selection of a first subset of the medical image data takes place by means of the at least one first filter unit 12. The first filter unit 12 includes at least one selection criterion with which the subset of the medical image data is determined. The subset can also include the original set of image data. For example, such selection criteria include (but not exclusively) DICOM (Digital Imaging and Communications in Medicine) attributes, thus attributes of an open standard for storage and exchange of information in medical image data management for instance properties of a contrast or orientation or other attributes (for instance points in time of a measurement), or information about an administration of contrast agent. Different attributes can differ in different levels of scalability; for example, they can be nominally, ordinally or cardinally scalable. For example, all image data that include a head as a body part can thus be selected.

This first subset of the medical image data is presented as an output by the output unit 15, for example a monitor. This presentation preferably occurs directly after the selection of the first subset of the medical image data by the at least one first filter unit. Via this type of preview, a user can directly detect the result of the application of the first filter to the output unit 15. The preview preferably takes place in real time, thus within a predefined, fixed time interval.

After the output of the first subset of the medical image data, a new selection of a new first subset of the medical image data can be made. The original selection is then discarded. After perceiving the result of the application of the first filter at the output unit 15, a user can thus adapt and/or refine the filter criteria. The method according to the invention thus repeats method step 3.

The processing of the first subset of the medical image data takes place in method step 4 by the at least one second filter unit 13, this processing leading to a second subset. The second filter unit 13 includes at least one processing rule with the aid of which the first subset of the medical image data is processed. For example, such processing rules include (but not exclusively) fusions, i.e. superpositions of image data and thus assemblies or merging of image data; or subtractions, i.e. rules with which pixel and/or voxel values from image data are subtracted from one another. The second subset of the medical image data can also entirely or partially include the first subset of the medical image data, for instance if the results after application of the second filter to the medical image data are added to the results of the application of the first filter to the medical image data.

In method step 5, sorting and/or grouping of the second subset of the medical image data is/are implemented by the processing unit 14. The sorting includes an organization according to a predeterminable criterion such as, for example, an acquisition point in time, an image size or other values. The result of the sorting is thus a sequence of image data. The grouping includes a classification of image data in at least one class. Image data are thereby associated with a class if they coincide in defined (likewise predeterminable) properties, for example an alignment. The sorting and/or grouping can also include the omission of defined image data, for example if only a specific number of image data is desired, for instance.

In method step 6, a presentation type for the second subset of the medical image data likewise is determined by the processing unit 14. The presentation type includes all possible forms of depicting image data, thus all possible layouts. The presentation type essentially includes a number of images that should be output to an output unit 15 and a mode of how the images should be output to the output unit 15, thus whether a screen content should be displaceable or not.

The determination of the presentation type of the medical image data includes the determination of an image format. An image format is predominantly the relationship of length to width of an image or of an image field. The presentation of the medical image data can thereby be optimized for the output unit 15 that is used.

The determination of the presentation type of the medical image data also includes a synchronization of the medical image data with regard to defined attributes. Synchronization is the establishment of defined properties for all medical image data of a defined type. For example, a predeterminable image section or zoom factor can be established for all image data with a defined orientation. In this way, the medical image data can be prepared such that, for example, the same image section is always perceivable, without such settings needing to be made manually for every image.

Finally, the determination of the presentation type of the medical image data includes a display of additional available information, for instance additional evaluations and/or examination results corresponding to the image data. This information can be mean value curves of dynamic contrast measurements, for example. However, this additional available information can also be information going beyond the image data information insofar these can be loaded from a database.

In method step 7, the presentation of the second subset of the medical image data according to a defined presentation type takes place by the output unit 15.

From the second subset of the medical image data, only an initial processed image can be presented as an output by means of the output unit 15. After the presentation of this initial processed image, a new determination of a presentation type can be made for the second subset of the medical image data and the original determination can be discarded. In this way, changes and/or refinements of the determination of the presentation type can be made in a time-saving manner. The method according to the invention thus repeats method step 6.

The reception of the medical image data and/or the selection of the first subset of the first medical image data and/or the processing and/or sorting and/or the grouping of the second subset of the medical image data and/or the determination of a presentation type for the subset of the medical image data and/or the output of the second subset of the medical image data according to a defined presentation type takes place automatically in the event that this is desired, or in the event that the same selection of parameters should always be selected in many embodiments of the method according to the invention.

Method step 8 designates the end of the preparation of medical image data of at least one medical imaging apparatus 9.

In summary, the invention concerns a control method for preparation of medical image data of at least one medical imaging apparatus, including the following steps:
 receive the medical image data by a reception unit,
 select a first subset of the medical image data by at least one first filter unit,
 process the first subset of the medical image data by at least one second filter unit, wherein the processing leads to a second subset,
 sort and/or group the second subset of the medical image data by a processing unit,
 determine a presentation type for the second subset of the medical image data by the processing unit, and
 present the second subset of the medical image data as an output according to a defined presentation type by means of an output unit.

Although modifications and changes may be suggested by those skilled in the art, it is the intention of the inventor to embody within the patent warranted hereon all changes and modifications as reasonably and properly come within the scope of his contribution to the art.

We claim as our invention:

1. A method for processing medical image data for display thereof, comprising:
 (a) providing medical image data to a computer, said medical image data comprising multiple medical images acquired in an image acquisition procedure having procedural attributes that each affect a content of said medical images;
 (b) in said computer, processing said medical image data in a first filter operated according to at least one first filter rule that limits said medical image data dependent on at least one of said procedural attributes, in order to obtain a first subset of said medical image data, said first subset comprising at least one image comprised of image elements selected from the group consisting of pixels and voxels;
 (c) at a display in communication with said computer, displaying a preview presentation of said first subset;
 (d) in said computer, receiving a manual input after displaying said preview presentation of said first subset, said manual input being selected from the group consisting of a modification of said first filter rule, and acceptance of said first subset displayed in said preview presentation;
 (e) when said manual input modifies said first filter rule, repeating (b) and (c) with the first filter operated according to the modified first filter rule;
 (f) repeating (b), (c), (d) and (e) until said manual input is acceptance of said preview presentation of said first subset;
 (g) in said computer, processing said first subset accepted in (f) in a second filter according to at least one second filter rule that specifies manipulation of said image elements of said at least one medical image in said first subset in order to obtain a second subset comprising medical image data with image elements thereof manipulated according to said at least one second filter rule;
 (h) in said computer, sorting or grouping said medical image data in said second subset dependent on a diagnostic criterion for making a diagnosis from said medical image data provided to said computer in (a);
 (i) in said computer, selecting a presentation mode for the sorted or grouped medical image data of said second subset;
 (j) at said display in communication with said computer, displaying a preview presentation of said second subset in the selected presentation mode;
 (k) in said computer, receiving a further manual input after displaying said preview presentation of said second subset, said further manual input being selected from the group consisting of a change of said selected presentation mode, and acceptance of display of said second subset with said selected presentation mode; and
 (l) repeating (j) and (k) until said further manual input is acceptance of display of said second subset.

2. A method as claimed in claim 1 comprising selecting said presentation mode to include an image format.

3. A control method as claimed in claim 1 comprising selecting said presentation mode to include a synchronization of said received medical image data with respect to defined attributes.

4. A control method as claimed in claim 1 comprising selecting said presentation type to include a display, at said display, of additional information relevant to said medical image data.

5. A control computer for preparing medical image data received from at least one medical imaging apparatus, comprising:

an input at which (a) medical image data are provided, said medical image data comprising multiple medical images acquired in an image acquisition procedure having procedural attributes that each affect a content of said medical images;

said computer being configured to (b) process said medical image data in a first filter operated according to at least one first filter rule that limits said medical image data dependent on at least one of said procedural attributes, in order to obtain a first subset of said medical image data, said first subset comprising at least one image comprised of image elements selected from the group consisting of pixels and voxels;

a display in communication with said computer at which said computer is configured to (c) display a preview presentation of said first subset;

said computer being configured to (d) receive a manual input after displaying said preview presentation of said first subset, said manual input being selected from the group consisting of a modification of said first filter rule, and acceptance of said first subset displayed in said preview presentation;

said computer being configured, when said manual input modifies said first filter rule, to (e) repeat (b) and (c) with the first filter operated according to the modified first filter rule;

said computer being configured to (f) repeat (b), (c), (d) and (e) until said manual input is acceptance of said preview presentation of said first subset;

said computer being configured to (g) process said first subset accepted in (f) in a second filter according to at least one second filter rule that specifies manipulation of said image elements of said at least one medical image in said first subset in order to obtain a second subset comprising medical image data with image elements thereof manipulated according to said at least one second filter rule;

said computer being configured to (h) sort or group said medical image data in said second subset dependent on a diagnostic criterion for making a diagnosis from said medical image data provided to said computer in (a);

said computer being configured to (i) select a presentation mode for the sorted or grouped medical image data of said second subset;

said computer being configured to (j) at said display in communication with said computer, display a preview presentation of said second subset in the selected presentation mode;

said computer being configured to (k) receive a further manual input after displaying said preview presentation of said second subset, said further manual input being selected from the group consisting of a change of said selected presentation mode, and acceptance of display of said second subset with said selected presentation mode; and said computer being configured to (l) repeat (j) and (k) until said further manual input is acceptance of display of said second subset.

6. A non-transitory, computer-readable data storage medium encoded with programming instructions, said storage medium being loaded into a control computer and said programming instructions causing said control computer to:

(a) receive medical image data, said medical image data comprising multiple medical images acquired in an image acquisition procedure having procedural attributes that each affect a content of said medical images;

(b) process said medical image data in a first filter operated according to at least one first filter rule that limits said medical image data dependent on at least one of said procedural attributes, in order to obtain a first subset of said medical image data, said first subset comprising at least one image comprised of image elements selected from the group consisting of pixels and voxels;

(c) at a display in communication with said computer, display a preview presentation of said first subset;

(d) receive a manual input after displaying said preview presentation of said first subset, said manual input being selected from the group consisting of a modification of said first filter rule, and acceptance of said first subset displayed in said preview presentation;

(e) when said manual input modifies said first filter rule, repeat (b) and (c) with the first filter operated according to the modified first filter rule;

(f) repeat (b), (c), (d) and (e) until said manual input is acceptance of said preview presentation of said first subset;

(g) process said first subset accepted in (f) in a second filter according to at least one second filter rule that specifies manipulation of said image elements of said at least one medical image in said first subset in order to obtain a second subset comprising medical image data with image elements thereof manipulated according to said at least one second filter rule;

(h) sort or group said medical image data in said second subset dependent on a diagnostic criterion for making a diagnosis from said medical image data provided to said computer in (a);

(i) select a presentation mode for the sorted or grouped medical image data of said second subset;

(j) at said display in communication with said computer, display a preview presentation of said second subset in the selected presentation mode;

(k) receive a further manual input after displaying said preview presentation of said second subset, said further manual input being selected from the group consisting of a change of said selected presentation mode, and acceptance of display of said second subset with said selected presentation mode; and (l) repeat (j) and (k) until said further manual input is acceptance of display of said second subset.

* * * * *